(12) United States Patent
Seville

(10) Patent No.: US 8,118,031 B2
(45) Date of Patent: Feb. 21, 2012

(54) HEARING PROTECTION DEVICE WITH DAMPED MATERIAL

(75) Inventor: Alan Seville, Indianapolis, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 581 days.

(21) Appl. No.: 11/335,412

(22) Filed: Jan. 19, 2006

(65) Prior Publication Data

US 2006/0162992 A1    Jul. 27, 2006

Related U.S. Application Data

(60) Provisional application No. 60/645,479, filed on Jan. 21, 2005.

(51) Int. Cl.
*A61F 11/00* (2006.01)
*H04R 25/00* (2006.01)

(52) U.S. Cl. .......................... 128/864; 181/129; 381/370

(58) Field of Classification Search .................. 128/864, 128/866, 867; 181/129, 130, 135; 381/370, 381/71.1, 71.6
See application file for complete search history.

(56) References Cited

U.S. PATENT DOCUMENTS

| 4,867,149 A | 9/1989 | Falco |
| 4,878,560 A | 11/1989 | Scott |
| 5,483,027 A | 1/1996 | Krause |
| 6,849,684 B2 * | 2/2005 | Poppe et al. .................. 524/539 |
| 2007/0183606 A1 * | 8/2007 | Doty ............................... 381/72 |

FOREIGN PATENT DOCUMENTS

| JP | 2005225988 | * | 2/2004 |
| WO | WO 02/26465 | | 4/2002 |
| WO | WO 02/26465 A1 | | 4/2002 |
| WO | WO 03/072623 A2 | | 9/2003 |

OTHER PUBLICATIONS

International Search Report; PCT/US2006/001822; May 29, 2006.
Written Opinion of International Searching Authority; PCT/US2006/001822.
Standard Parts Catalog and Engineering Design Guide from Aearo Technologies, a 3M Company (2005).
ISODAMP® 8002 Series Product Information for Thermoplastic Elastomer Molding Material from Aearo Company (2005).
Non-Halogenated Product Information for ISODAMP® C-8000 Materials, ISOLOSS® SL Materials, and CONFOR® EG Foams from Aearo Technologies, a 3M Company (2007).
European Search Report dated Oct. 22, 2010 for European Application No. 10010770.

* cited by examiner

*Primary Examiner* — Patricia Bianco
*Assistant Examiner* — Tarla Patel
(74) *Attorney, Agent, or Firm* — Eric D. Levinson

(57) ABSTRACT

The invention provides a hearing protection device having an attenuating body composed of an elastomer with an increased glass transition temperature and a reduced glass-to-rubber transition temperature such that the damping factor of the material peaks at a higher temperature and, resultantly, the damping factor is increased over a range of temperatures and frequencies typically experienced by the device during usage. The increased damping results in higher sound attenuation provided by the hearing protection device.

26 Claims, 4 Drawing Sheets

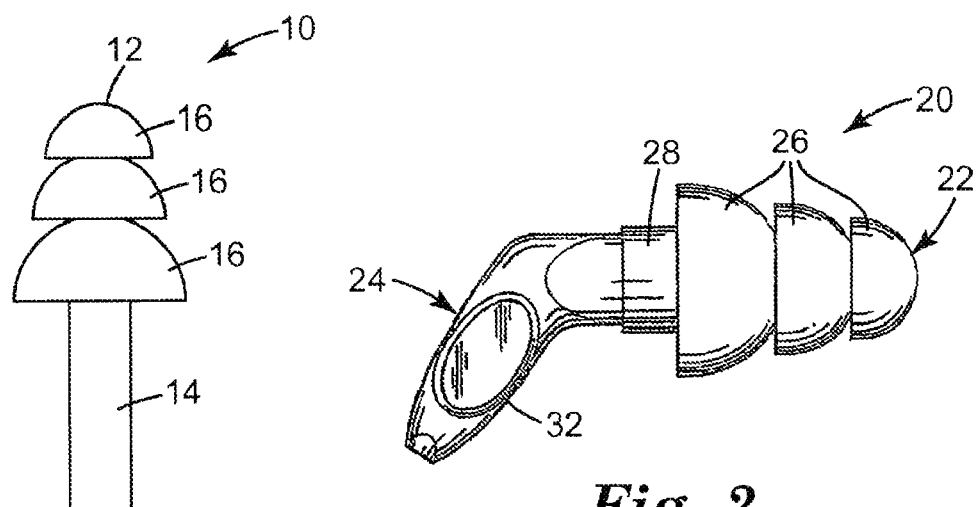
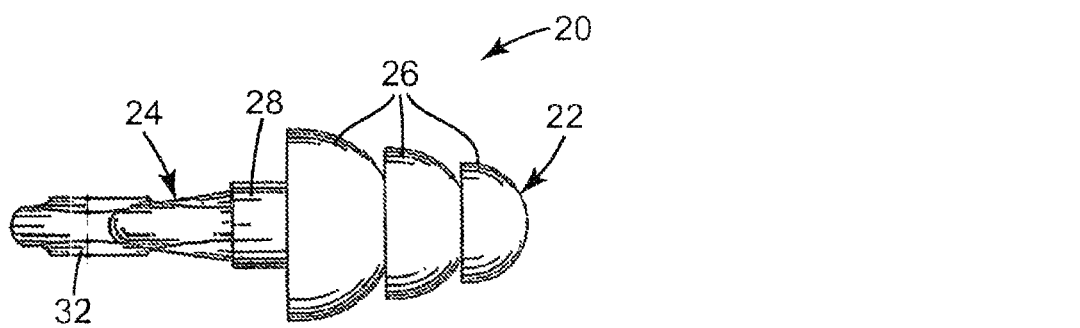
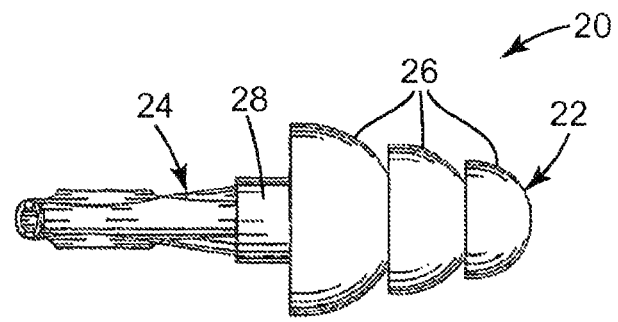
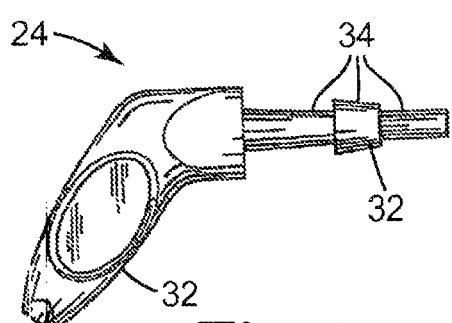

HEARING PROTECTION DEVICE WITH DAMPED MATERIAL

CROSS REFERENCE TO RELATED APPLICATIONS

This application is related to and claims the benefit of U.S. Provisional Patent Application Ser. No. 60/645,479 filed on Jan. 21, 2005, the entire contents of which are herein incorporated by reference.

TECHNICAL FIELD OF INVENTION

The invention generally concerns hearing protection devices and, more particularly, hearing protection devices composed at least partially of a damped material for providing enhanced sound attenuation.

BRIEF DISCUSSION OF RELATED ART

The need for individual hearing protection in industrial and other occupational and recreational settings is well established. The prior art is replete with hearing protection devices, including earplugs, earmuffs, semi-insert devices, full-head helmets, etc. Such devices are intended to be worn over a user's ear, or are inserted at least partially within the earcanal, to thus prevent sounds from reaching the inner ear at undesirably high levels.

Earplugs include any of a variety of devices designed to be inserted into the earcanal and are often preferred for providing high attenuation while being discrete and comfortable when worn. Earplugs generally may be categorized as either "roll-down" or "push-in".

Roll-down type earplugs are typically compressible, slow-recovery foam earplugs which must be compressed, or "rolled down", by the user prior to insertion into the earcanal. Typical roll-down earplugs are disclosed in U.S. Pat. No. 6,105,715 to Knauer, herein incorporated by reference in its entirety. Such roll-down earplugs are often composed of a homogenous slow recovery polyvinyl chloride (PVC) or polyurethane (PU) material and include a substantially circular cross-section which is larger than a cross-section of the average earcanal. The roll-down type earplugs are compressed before insertion to reduce the cross-section and thus allow insertion thereof into the earcanal. Once inserted, the compressed roll-down earplug expands to occlude the earcanal and thus block the passage of sound into the inner ear.

"Push-in" type earplugs generally comprise an attenuating portion and a rigid or semi-rigid portion typically extending therefrom or embedded therein. The sound attenuating portion is typically formed of a soft conformable material; the rigid or semi-rigid portion may be composed of any material, such as a plastic or a rubber, with sufficient rigidity as required. Push-in type earplugs are often preferred for their ease of insertion. Unlike roll-down type earplugs, push-in plugs do not have to be compressed prior to insertion. The user simply grasps the rigid or semi-rigid portion and inserts the attenuating portion into the earcanal. Here, the rigid or semi-rigid portion is utilized to push the sound attenuating portion into position within the earcanal. Upon insertion, the sound attenuating portion conforms to the contours of the earcanal and thus occludes the earcanal to therefore inhibit the passage of sound therethrough. Thus, push-in type earplugs provide for a more convenient insertion process than roll-down type earplugs. Additionally, push-in earplugs are often preferred for their hygienic properties over roll-down plugs. That is, push-in earplugs only require handling of the rigid or semi-rigid portion during insertion. This minimizes the transfer of substances (e.g., dirt, oil, etc.) from the fingers to the attenuating portion, thus reducing the likelihood that such substances are exposed to the earcanal.

Roll-down and push-in type earplugs are routinely tested for their ability to block sound in a human earcanal. This ability to block sound or attenuate is measured in accordance with the established testing procedures such as that set forth in the American National Standards Institute's, "Method for the Measurement of Real-Ear Protection of Hearing Protectors and Physical Attenuation of Earmuffs", ANSI S3.19-1974. In this test, Real-ear Attenuation at Threshold (REAT) testing is conducted in a laboratory test chamber which is a semi-reverberant, double-walled, structurally isolated room using third-octave bands of noise as test signals. A human subject responds to the test signals at her/his threshold, i.e. as soon as the subject can detect the signals, in both Open (nothing in or around the ears) and Occluded (hearing protector in the ears) conditions. The difference in sound pressure level (SPL) between the two conditions is the attenuation afforded by the Hearing Protector. This difference is recorded in decibels of attenuation provided by the hearing protector at a given frequency. Data obtained from this test method is then used to calculate a single number rating (NRR) which provides a number which is then used to label the product. In most instances there is thus a desire to develop products with higher NRR values.

Roll-down type earplugs often exhibit a higher NRR than comparable push-in type earplugs. However, this higher NRR is dependent upon a proper insertion of the earplug into the earcanal. As mentioned above, insertion of roll-down type earplugs can be more complicated and perhaps more time consuming than insertion of push-in type earplugs. Additionally, due to the foam material construction, roll-down type earplugs often have shorter usage lifetime than push-in earplugs. Push-in plugs, on the other hand are easily insertable and have a longer usage lifetime but are often associated with lower NNRs than comparable roll-down type earplugs.

Attempts have been made to increase the NRR provided by push-in type earplugs. These attempts have focused on varying the design or construction of push-in earplugs to attain a better fit or seal within the earcanal. However, these new constructions have resulted in only moderately increased NRRs and at the sacrifice of comfort to the user.

Accordingly, a hearing protection device, particularly a push-in type earplug, is desired which provides a high degree of sound attenuation, is simple to use, is comfortable to the user, and has a long usage lifetime.

BRIEF SUMMARY OF THE INVENTION

The above discussed and other problems and deficiencies of the prior art are overcome or alleviated by the invention which provides a novel and nonobvious hearing protection device.

Generally, the invention comprises a sound attenuating device composed at least partly of a highly damped material. More particularly, the invention provides a hearing protection device having an attenuating body composed of an elastomer with an increased glass transition temperature and a reduced glass-to-rubber transition temperature such that the damping factor of the material peaks at a higher temperature and, resultantly, the damping factor is increased over a range of temperatures and frequencies typically experienced by the device during usage. The increased damping results in higher sound attenuation provided by the hearing protection device.

BRIEF DESCRIPTION OF THE DRAWINGS

Referring now to the several drawings:

FIG. 1 shows an exemplary hearing protection device according to the invention.

FIG. 2 is a side view of a hearing protection device in another embodiment of the invention;

FIG. 3 is a top view thereof;

FIG. 4 is a bottom view thereof; and

FIG. 5 is a side view of a stem portion of the hearing protection device of FIG. 2.

DETAILED DESCRIPTION OF THE INVENTION

Figure 6:
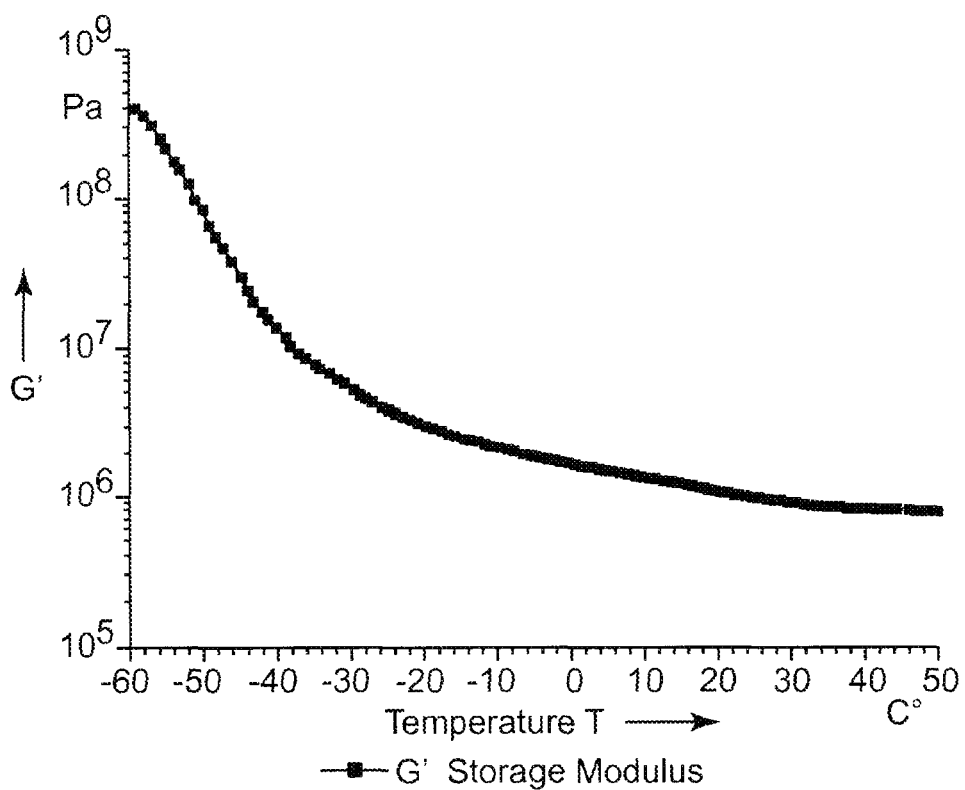
FIG. 6 is a graph of the storage modulus versus temperature for a sample according to the prior art.

FIG. 1 shows a push-in type earplug 10 in accordance with one embodiment of the invention. The earplug 10 includes a sound attenuating portion 12 disposed generally at one end of the earplug 10 and a stem portion 14 disposed at an opposite end of the earplug 10 extending in a direction away from the sound attenuating portion 12. The sound attenuating portion generally includes a plurality of rearwardly directed hemispherical or semi-hemispherical flange elements 16. In this embodiment, the sound attenuating portion 12 includes three generally hemispherical flange elements 16 of radially increasing size, as shown in the drawing. The earplug 10 is generally of the type disclosed in U.S. Pat. No. 4,867,149 granted on 19 Sep. 1989 to Falco, which is herein incorporated by reference in its entirety.

The earplug 10 is made of a conformable molded material of low resilience. Preferably, the sound attenuating portion 12 and the stem portion 14 are formed integrally of the same molded material. That is, the earplug 10 is formed in a single molding operation. However, in another embodiment of the invention, the earplug 10 may be formed non-integrally, i.e., the stem portion 14 may be formed first and then the sound attenuating portion 12 may be formed thereon or affixed thereto, etc. Additionally, if desired, the sound attenuating portion 12 and stem portion 14 may be formed of different materials.

Significantly, the material(s) forming the earplug 10 comprises a compound which exhibits significant damping properties over a range of temperatures and over a range of frequencies corresponding, respectively, to temperatures and frequencies experienced by the earplug during typical usage. The significant damping properties are exhibited, for example at temperatures of −20° C. to 50° C. and over frequencies of 125-8000 Hz.

In a preferred embodiment, the material composing the earplug is an elastomer which has a damping factor (tan δ) of approximately 1.0-0.05 over a temperature range of approximately 10-50° C. at a frequency of approximately 1 Hz, where tan δ is equivalent to the ratio of loss modulus to storage modulus. Even more preferably, the damping factor of the elastomer is approximately 0.10-0.30 over a temperature range of approximately 20-40° C. at a frequency of approximately 1 Hz. Specifically, the damping factor may be about 0.10 at about 40° C. and above about 0.30 at approximately 20° C. Additionally, the damping factor of the elastomer material increases as the frequency increases. Generally, for every magnitude increase in frequency, the damping increases to that associated with a 10° C. drop in temperature. For example, the damping factor of the material at 10 Hz, 20° C. is approximately equivalent to the damping factor at 1 Hz, 10° C.

Of course, these illustrative approximations are provided by way of example and are not intended to limit the scope of the invention in any way. In a more general sense, the material composing the earplug 10 comprises an elastomer having an increased glass transition temperature and a reduced glass-to-rubber transition temperature such that the damping factor of the material peaks at a higher temperature and, resultantly, the damping factor is increased over a range of temperatures and frequencies typically experienced by the earplug during usage.

The material may be any elastomeric material including the damping properties as discussed herein. An elastomer, as herein described, refers generally to any material which has the ability to undergo deformation under the influence of a force and substantially regain its original shape once the force has been removed. In a preferred embodiment, the material is a thermoplastic resin, such as a polyvinyl chloride (PVC) formulation, comprising a high molecular weight resin and a polymeric plasticizer which are utilized to shift the glass transition and glass-to-rubber transition temperatures as discussed to provide enhanced damping. The high molecular weight resin, for example, may be one which includes a higher relative viscosity than approximately 2.5. The high molecular weight resin is, for example, a resin such as that distributed under the trade name FORMALON NV. The plasticizer, for example, may be one which includes an average molecular weight higher than approximately 800. The plasticizer is, for example, a plasticizer distributed under the brand name ADMEX® 523.

This preferred PVC material is of course exemplary. The resin and plasticizer, and/or similar components, may be added to any number of base materials to provide the damping effect of the invention. For instance, the material used to compose the earplug 10 may include a damped version of one or more of the following: natural rubber, neoprene rubber, SBR rubber, silicone rubber, EPDM rubber, polybutadiene rubber, polyurethane elastomers, ethylene vinyl acetate elastomers, elastomers based on acrylic acid precursors, vinyl halide polymers, thermoplastic silicone rubber compositions, thermoplastic SBR block copolymers, SEBS block polymers, etc.

Advantageously, the damped earplug 10, when inserted into the earcanal of a user, provides an increase in sound attenuation over a broad range of frequencies. The increased sound attenuation provided by the earplug 10 indicates a projected NRR of approximately 3 dB. This higher attenuation is primarily provided because the increased damping properties of the earplug 10 tend to damp the vibration of the earplug within the earcanal and thus inhibit the transmission of sound to the inner ear of the user.

Example

Two material samples were subjected to dynamic mechanical analysis, torsional-type testing. The first sample (Sample 1) was composed of an elastomer resin conventionally used in pre-molded, push-in type earplugs. The second sample (Sample 2) was composed of a damped material in accordance with the present invention. Both samples were configured as bars having dimensions of approximately two inches by one-half inch by one-eighth inch. One end of the samples was fixed while the other end was torsionally oscillated at a frequency of 1 Hz over a specified temperature range (−60° C. to 50° C. for Sample 1, and −30° C. to 50° C. for Sample 2) with the strain at the extremes being 0.3%. The force required to twist each sample was recorded in relation to the storage modulus and the force required to return the sample to the untwisted state was recorded in relation to the loss modulus. The damping factor (tan δ) was then calculated for each sample.

The storage modulus determined for Sample 1 by way of the described testing is represented graphically in FIG. 6.

Here, the glass region of Sample 1 is just below −60° C. and the rubbery region starts around 20-30° C.

Figure 7:
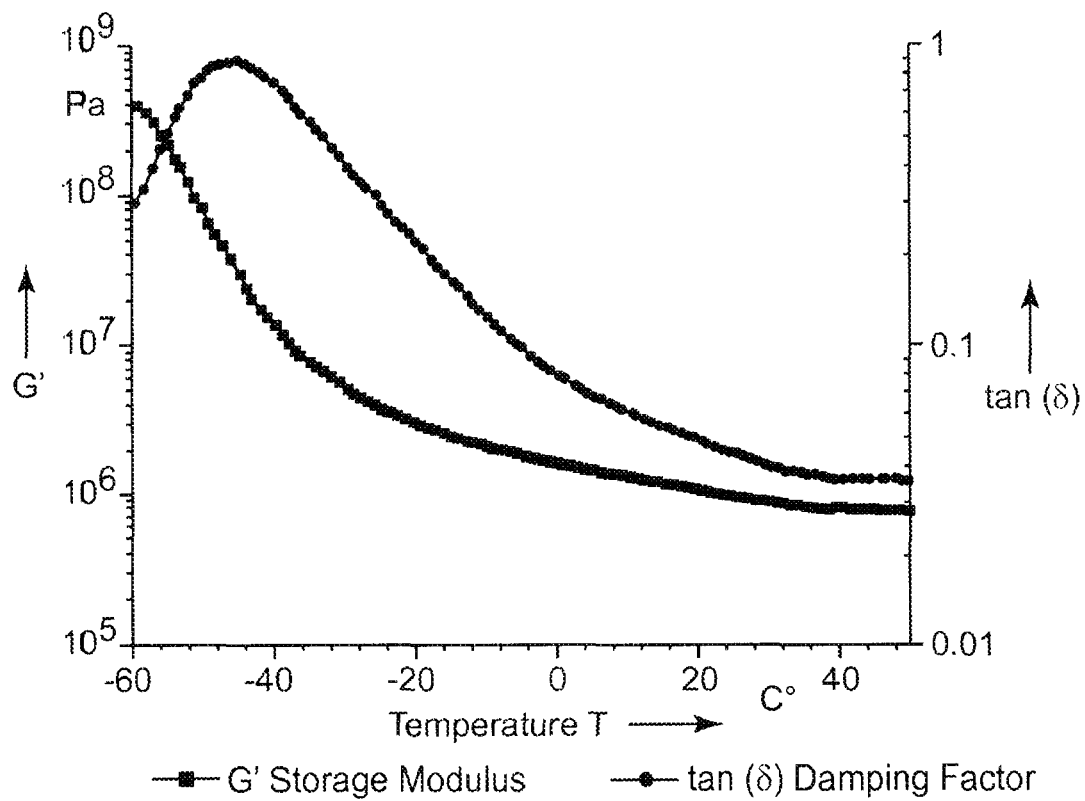
FIG. 7 is a graph of the damping factor and storage modulus versus temperature for the prior art sample used in FIG. 6.

The damping factor of Sample 1 is represented graphically in FIG. 7 along with the storage modulus from the graph shown in FIG. 6.

The damping factor of Sample 1 peaks at a very low temperature and thus is very low in the range of temperatures (20-40° C.) corresponding to typical use temperatures.

Figure 8:
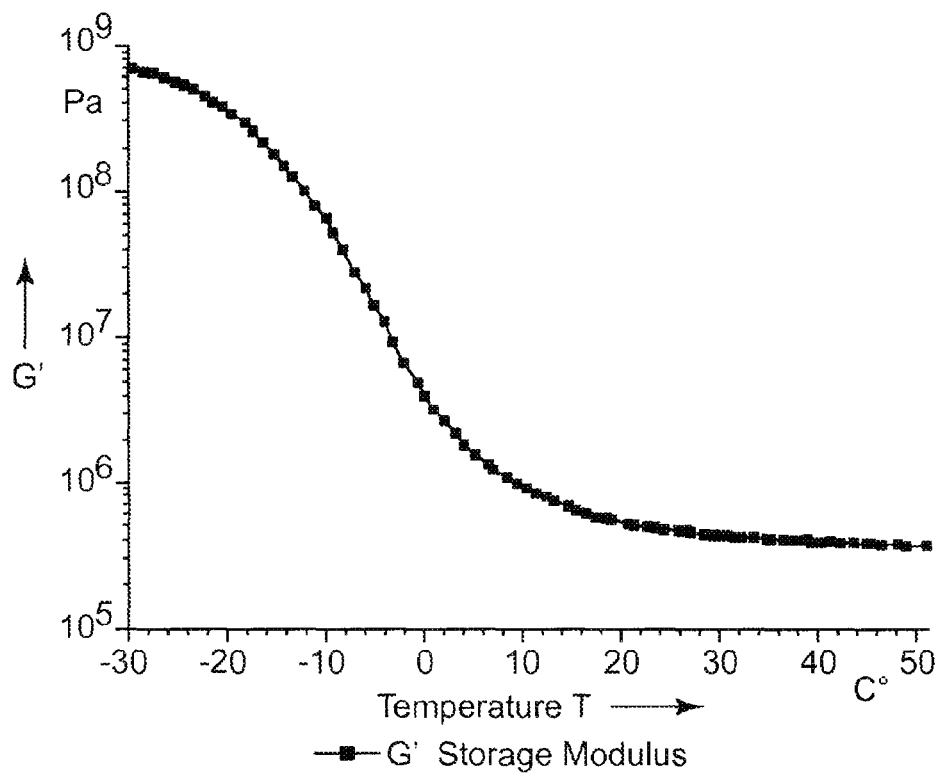
FIG. 8 is a graph of the storage modulus versus temperature for a sample according to the present invention.

The storage modulus determined for Sample 2 by way of the above-described testing is represented graphically in FIG. 8.

Figure 9:
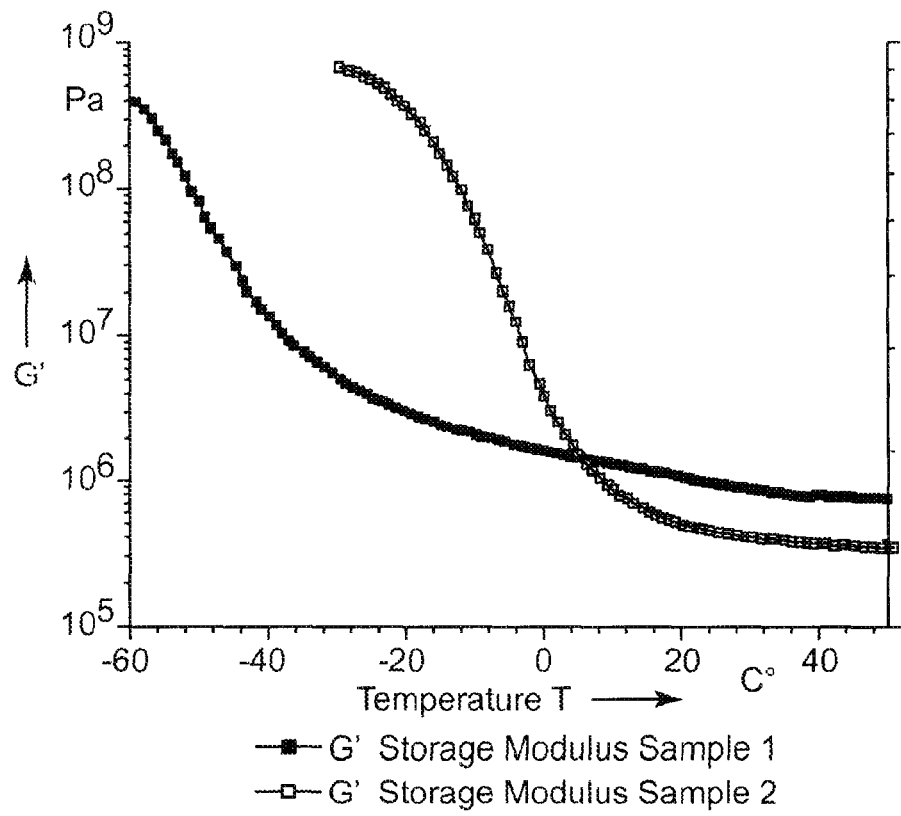
FIG. 9 is a graph of the storage modulus versus temperature for the two samples referred to above.

The graph shown in FIG. 9 represents the storage modulus of both Samples 1 and 2 and illustrates the increased glass transition and glass-to-rubber transition temperatures of Sample 2 over that of Sample 1.

Figure 10:
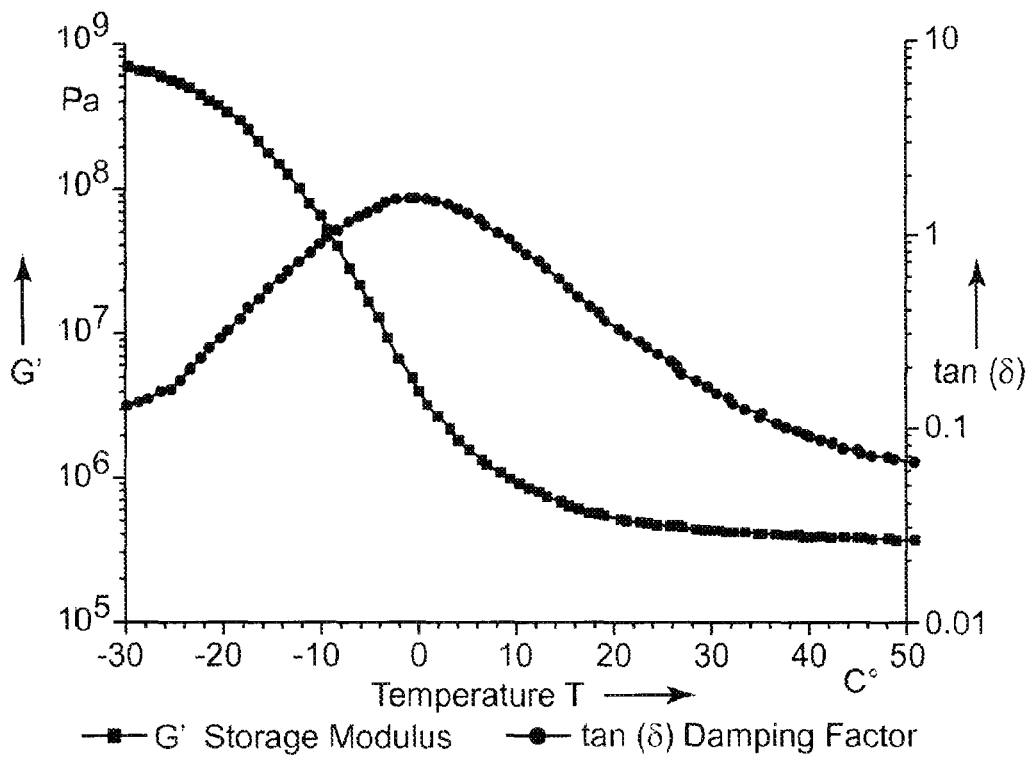
FIG. 10 is a graph of the damping factor and storage modulus versus temperature for the two samples referred to above.

This graph shown in FIG. 10 is a plot of the storage modulus and damping factor of Sample 2 and illustrates the heightened damping factor in the usable temperature range (20-40° C.).

Figure 11:
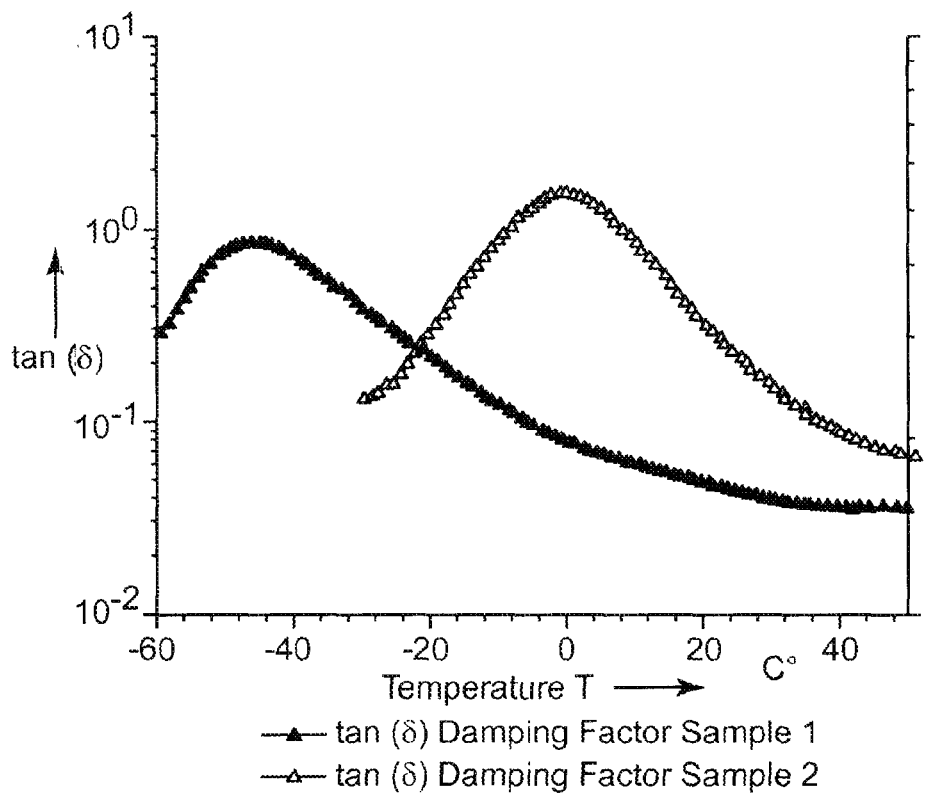
FIG. 11 is a graph of the damping factor versus temperature for the two samples referred to above.

This plot shown in FIG. 11 shows a comparison of the damping factors of Samples 1 and 2.

Clearly, Sample 2 exhibits increased damping properties over Sample 1. For reasons discussed above, this results in increased sound attenuation provided by a hearing protection device formed of the material of Sample 2.

The invention thus far has been described in terms of the earplug 10 of FIG. 1. However, this description serves only by way of example. The earplug 10 may take any shape desirable for providing hearing protection. For example, the earplug 10 may include one, two, or more than three flange elements 16, the stem portion 14 may be embedded in or fixed to one or more of the flange elements 16, the earplug 10 may not include a stem portion 14, etc. Alternatively, the hearing protector may comprise a semi-insert device where the damped material enhances the sound attenuation of the semi-inserted portion of the device.

As discussed herein above, in the embodiment of FIG. 1, the earplug 10 includes the stem portion 14 extending rearwardly from the sound attenuating portion 12. In this manner, the stem portion 14 serves as a handle when inserting, removing, or otherwise manipulating the earplug 10. It is advantageous to provide a degree of rigidity to the stem portion 14 in order to facilitate the insertion of the relatively softer, damped flange elements 16 into the earcanal of a wearer. That is, a degree of rigidity imparted upon the stem portion 14 allows the wearer to more easily and consistently push the damped flange elements 16 into the earcanal during the insertion process.

As mentioned above, the stem portion 14 may be formed integrally with the sound attenuating portion 12 or the stem portion 14 may be formed separately from the sound attenuating portion 12 and then affixed thereto by one of various methods. In FIG. 1, the earplug 10 includes the stem portion 14 being formed integrally with the sound attenuating portion 12. In this embodiment, the stem portion 14 may further include a stiffening element to provide the desired increased degree of rigidity. For example, the stiffening element may comprise a rigid or semi-rigid element that is received and retained within a receptacle formed in the stem portion 14. Alternatively, the stem portion may simply be formed, e.g. molded, about the rigid or semi-rigid element such that the element is disposed at a core of the stem portion. The rigid or semi-rigid element possesses an increased rigidity relative to the softer, damped material which is used to mold the stem portion 12 and the flange elements 16. Thus, the stiffening element imparts a degree of rigidity to the earplug 10 which facilitates insertion thereof.

As mentioned, the stem portion may alternatively be formed separately from the sound attenuating portion and then affixed thereto in order to form the earplug of the invention. Here again, the stem portion may include the stiffening element disposed within the stem portion, as discussed immediately above, in order to provide a certain stiffness to the earplug.

In another embodiment, the stem portion may simply be formed of a material which possesses a greater stiffness than the soft, damped material used to form the sound attenuating portion 12. Such a stiff stem portion is then affixed to the attenuating portion in order to form an earplug having a soft, damped attenuating portion and a more rigid stem portion.

For example, FIGS. 2-5 show an earplug 20 having a sound attenuating portion 22 and a stem portion 24 which are separately formed of materials of varying stiffness and then attached together to form the earplug 20. The attenuating portion 22 is formed of the damped material discussed herein above and includes one or more semi-hemispherical flange elements 26, similar to the flange elements 16 discussed above with regard to FIG. 1. The attenuating portion 22 further includes a cuff 28 which facilitates in attaching the sound attenuating portion 22 to the stem portion 24. In this regard, the attenuating portion 22 includes a receptacle at its core which extends from the cuff 28 toward the foremost flange element 16. The stem 24 includes an insertion portion 30 and an opposing handle portion 32. The insertion portion 30 is configured to be received and retained within the receptacle of the sound attenuating portion 22. The insertion portion 30 may optionally include features 34 which aid in fixing the sound attenuating portion 22 to the insertion portion 30. For example, the features 34 may comprise surfaces configured to receive a bonding agent or surfaces configured to provide a friction or snap when engaged with the attenuating portion 22, etc. The handle portion 32 extends from the insertion portion 30 to provide an area for the wearer to grip and manipulate the earplug 20. Here, the handle portion 32 curves away from the insertion portion 30, as shown in the drawings. In one embodiment, the stem portion 24 is that disclosed in U.S. patent application Ser. No. 11/270,053 to Falco filed on Nov. 9, 2005, the entire contents of which are herein incorporated by reference.

As mentioned, the attenuating portion 22 of the earplug 20 is formed of the damped material of the invention. The stem portion 24 of the earplug 20 is formed of a plastic or a rubber material and may be formed through a molding process, and particularly, by an injection molding process. Importantly, the stem portion 24 is formed of a material having a certain degree of rigidity in order to impart a desired stiffness to the earplug 20. Thus, in this manner, the earplug 20 comprises a softer sound attenuating portion 22 formed of the damped material which provides enhanced comfort and high attenuation to the wearer. Further, the earplug 20 comprises the relatively more rigid stem portion 24 which aids in inserting and removing the earplug 20 relative to the earcanal of the wearer.

The illustrated shape and size of the stem portion 24 is shown in the drawings by way of example only. In another embodiment, the stem portion 24 comprises a straight element which extends rearwardly from the attenuating portion 22 along a longitudinal axis thereof. In still another embodiment, the stem portion 24 includes linear and/or curvilinear features such that the stem portion 24 may extend along the longitudinal axis or diverge therefrom, as desired.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A hearing protection device, comprising:
a sound attenuating body of the device;
wherein the body is composed at least partially of a material having a damping factor of approximately 0.10-0.30 over a temperature range of approximately 20-40° C. at a frequency of approximately 1 Hz.

2. The hearing protection device of claim 1, wherein the material comprises an elastomer and wherein the damping factor is provided, at least in part, by use of the elastomer of a high molecular weight resin and a polymeric plasticizer.

3. The hearing protection device of claim 1, wherein the damping factor at 1 Hz is approximately 0.10 at 40° C. and above about 0.30 at 20° C.

4. The hearing protection device of claim 1, wherein the body comprises a sound attenuating portion of an earplug.

5. The hearing protection device of claim 4, further comprising an elongated stem portion attached at least at one end to the sound attenuating portion, wherein the stem portion includes a stiffness greater than a stiffness of the sound attenuating portion.

6. The hearing protection device of claim 5, wherein the sound attenuating portion comprises a plurality of semi-hemispherical flanges which extend radially from the stem portion in a rearward direction.

7. The hearing protection device of claim 4, wherein the sound attenuating portion is disposed on a band worn proximate to the head or neck of a user.

8. The hearing protection device of claim 1, wherein the material composing the body comprises SBR or SEBS.

9. A hearing protection device, comprising:
an attenuating body composed of an elastomer having an increased damping property provided by use of a high molecular weight resin and a polymeric plasticizer;
wherein the resin and plasticizer increase a glass transition temperature of the elastomer and reduce a glass-to-rubber transition temperature of the elastomer such that a damping factor of the material peaks at an increased temperature.

10. The hearing protection device of claim 9, wherein the damping property is increased over a range of temperatures corresponding to temperatures which the earplug is exposed to when worn by a user.

11. The hearing protection device of claim 10, wherein the range of temperatures is approximately 20° C. to 40° C.

12. The hearing protection device of claim 9, wherein the damping factor peaks at approximately 0° C. at 1 Hz.

13. The hearing protection device of claim 9, wherein the damping factor at 1 Hz is approximately 0.10 at 40° C. and above about 0.30 at 20° C.

14. The hearing protection device of claim 9, wherein the body comprises a sound attenuating portion of an earplug.

15. The hearing protection device of claim 14, further comprising an elongated stem portion attached at least at one end to the sound attenuating portion, wherein the stem portion includes a stiffness greater than a stiffness of the sound attenuating portion.

16. The hearing protection device of claim 15, wherein the sound attenuating portion comprises a plurality of semi-hemispherical flanges which extend radially from the stem portion in a rearward direction.

17. The hearing protection device of claim 14, wherein the sound attenuating portion is disposed on a band worn proximate to the head or neck of a user.

18. A hearing protection device, comprising:
an attenuating body composed of a material having an increased damping property provided by use of a damped SBR or SEBS;
wherein the damped SBR or SEBS material has an increased glass transition temperature and a reduced glass-to-rubber transition temperature such that a damping factor of the material peaks at an increased temperature.

19. The hearing protection device of claim 18, wherein the damping property is increased over a range of temperatures corresponding to temperatures which the earplug is exposed to when worn by a user.

20. The hearing protection device of claim 19, wherein the range of temperatures is approximately 20° C. to 40° C.

21. The hearing protection device of claim 18, wherein the damping factor peaks at approximately 0° C. at 1 Hz.

22. The hearing protection device of claim 18, wherein the damping factor at 1 Hz is approximately 0.10 at 40° C. and above about 0.30 at 20° C.

23. The hearing protection device of claim 18, wherein the attenuating body comprises a sound attenuating portion of an earplug.

24. The hearing protection device of claim 23, further comprising an elongated stem portion attached at least at one end to the sound attenuating portion, wherein the stem portion includes a stiffness greater than a stiffness of the sound attenuating portion.

25. The hearing protection device of claim 23, wherein the sound attenuating portion comprises a plurality of semi-hemispherical flanges which extend radially from the stem portion in a rearward direction.

26. The hearing protection device of claim 23, wherein the sound attenuating portion is disposed on a band worn proximate to the head or neck of a user.

* * * * *

UNITED STATES PATENT AND TRADEMARK OFFICE
CERTIFICATE OF CORRECTION

| | |
|---|---|
| PATENT NO. | : 8,118,031 B2 |
| APPLICATION NO. | : 11/335412 |
| DATED | : February 21, 2012 |
| INVENTOR(S) | : Alan R Seville |

It is certified that error appears in the above-identified patent and that said Letters Patent is hereby corrected as shown below:

<u>Column 2</u>
Line 40, delete "NNRs" and insert -- NRRs --, therefor.

Signed and Sealed this
Sixth Day of November, 2012

David J. Kappos
*Director of the United States Patent and Trademark Office*